United States Patent [19]
Reitknecht

[11] 3,938,898
[45] Feb. 17, 1976

[54] SWAB APPLICATOR WITH ADAPTER CHUCK AND CLOSURE

[76] Inventor: Jack Reitknecht, 210 E. Broadway, New York, N.Y. 10002

[22] Filed: Apr. 5, 1974

[21] Appl. No.: 458,449

[52] U.S. Cl. .................. 401/183; 128/269; 401/207
[51] Int. Cl.[2] .......................................... B05B 11/00
[58] Field of Search .......................... 401/183–185, 401/196, 207, 132, 133; 128/269; 401/261, 262

[56] References Cited
UNITED STATES PATENTS

| | | | |
|---|---|---|---|
| 1,007,492 | 10/1911 | Ruch | 401/262 |
| 2,119,646 | 6/1938 | Pidec | 401/207 |
| 2,168,179 | 8/1939 | Tobey | 401/207 X |
| 2,312,136 | 2/1943 | Van Triest | 401/92 X |
| 3,106,741 | 10/1963 | Stoner | 401/183 |
| 3,481,676 | 12/1969 | Schwartz et al. | 401/196 X |
| 3,759,259 | 9/1973 | Truhan | 401/132 X |
| 3,792,699 | 2/1974 | Tobin | 128/269 |

*Primary Examiner*—Lawrence Charles
*Attorney, Agent, or Firm*—Clarence O'Brien; Harvey B. Jacobson

[57] ABSTRACT

A swab or applicator utilizing a generally pliable or bendable tubular member of plastic or similar material having one end inserted into and gripped by a gripping chuck and the other end provided with an absorbent swab of cotton or other natural or synthetic material with a passage being exposed at the tip end of the swab for discharging material therethrough and applying such material to a desired location. The inner end of the tubular member is beveled and provided with roughened surface area portions to facilitate the gripping thereof. Various chuck adapters mount the tubular member on containers having structural characteristics enabling the contents of the container to be discharged from the opening in the tip end of the swab. A closure disk is provided in the chuck adapter to maintain the contents of the container sealed until ready for use.

6 Claims, 9 Drawing Figures

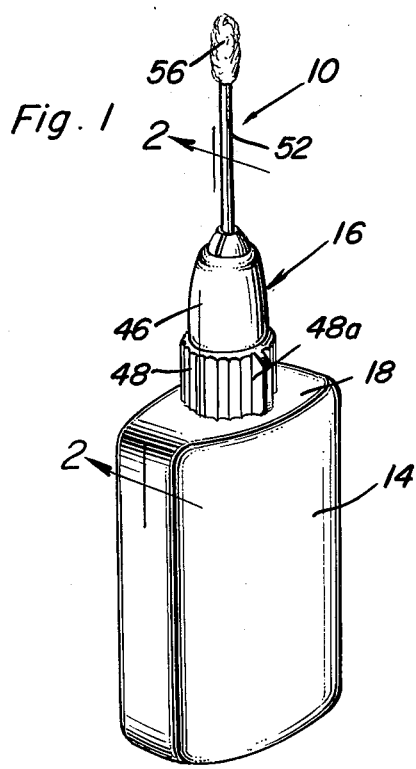
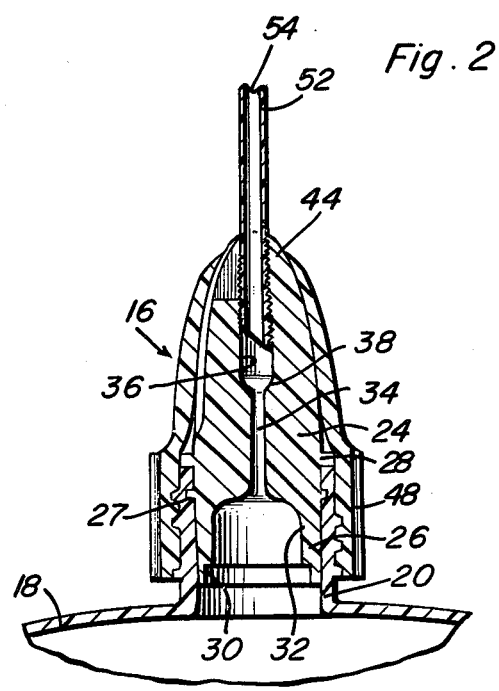
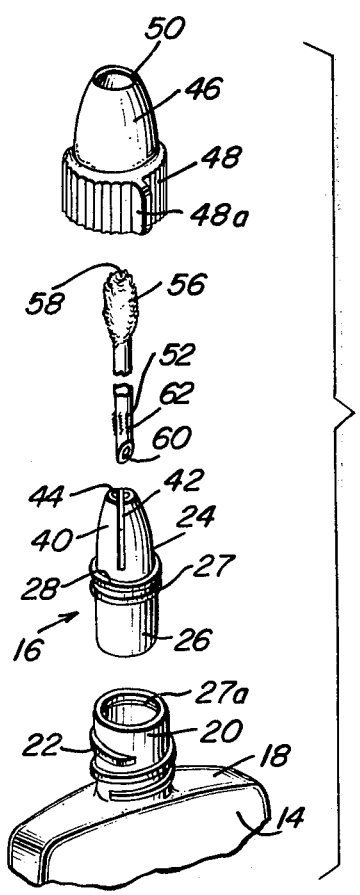
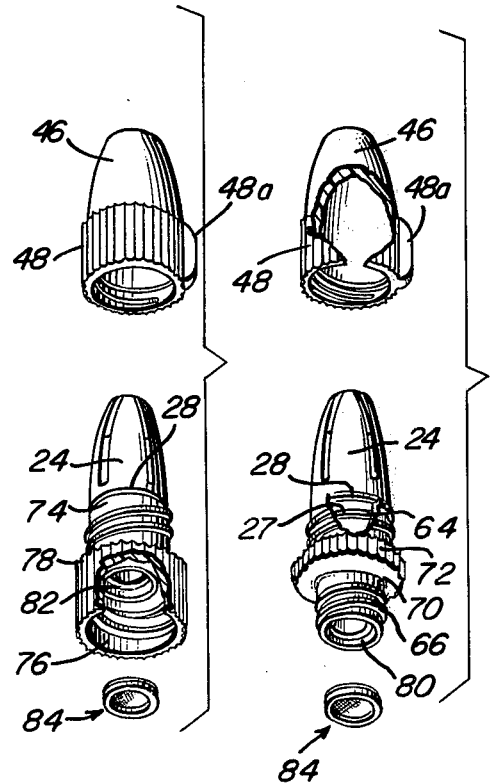

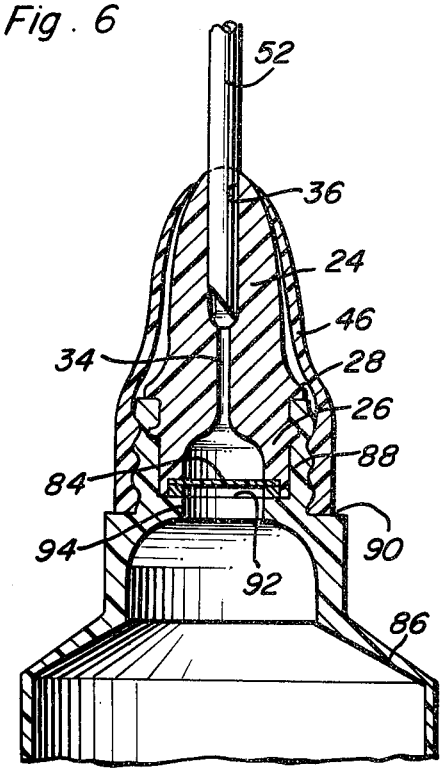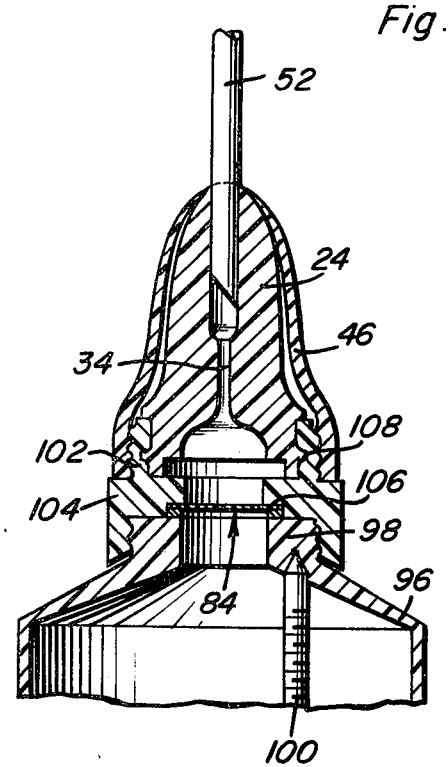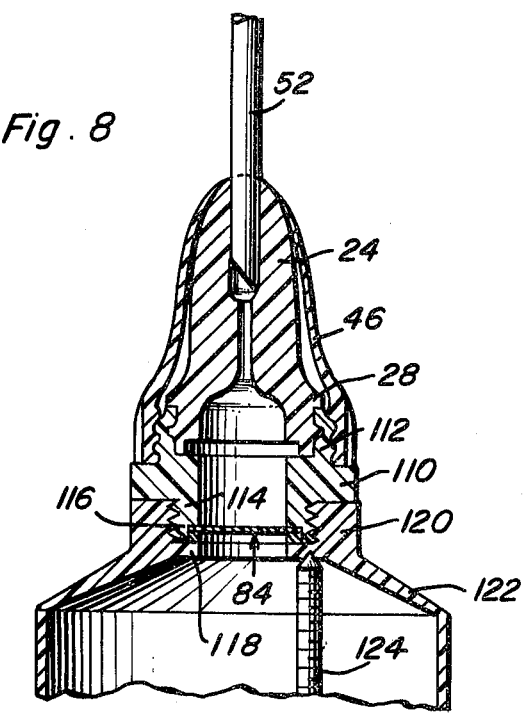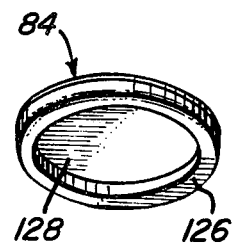

3,938,898

SWAB APPLICATOR WITH ADAPTER CHUCK AND CLOSURE

BACKGROUND OF THE INVENTION

1. Field of the Invention

The present invention generally relates to swabs or applicators for applying solutions to various surfaces and the like where an absorbent swab is desired with the invention more particularly relating to the specific construction of the swab, a chuck adapter for mounting the swab on a container and a closure member for the container to seal the contents thereof during periods of non-use.

2. Description of the Prior Art

Swabs with absorbent tips are used in many instances for applying solutions, ointments and the like onto various surface areas such as various areas of the human anatomy. Such devices are also used for cleaning such surface areas, gently massaging such areas and the like. It is also well known to provide various types of containers which have a dispensing function. Typical of such containers are squeezable bottles or containers constructed of plastic material such that the container may be squeezed to dispense material through a discharge opening. Other containers of this type are those which have a manually operated mechanism for dispensing a predetermined quantity of material such as found in my prior U.S. Pat. Nos. 3,039,476, issued June 19, 1962 and 3,728,035, issued Apr. 17, 1973. While such squeeze bottles and manually operated dispensing mechanisms are utilized extensively and perform satisfactorily for their particular purposes, such devices have limitations in their utility under certain circumstances.

SUMMARY OF THE INVENTION

An object of the present invention is to provide a swab and applicator incorporating a tubular member of plastic material having a passageway therethrough and provided with an absorbent swab at the tip end thereof with the passageway being exposed or open to the tip end for discharge of material onto a surface.

Another object of the invention is to provide a swab or applicator in accordance with the preceding object in which the end of the tubular member remote from the absorbent swab is received in, gripped by and supported by a gripping chuck mounted on a container having a quantity of flowable material therein for discharge from the tip end of the swab.

A further object of the invention is to provide a swab and applicator in accordance with the preceding objects in which the chuck adapter is provided with a rupturable seal in the form of a disk which maintains the flowable material in the container sealed prior to discharge.

Still another object of the invention is to provide a swab or applicator in which the chuck adapter is constructed in different embodiments to enable association with containers having various structural characteristics.

A still further object of the invention is to provide a swab or applicator in which the chuck adapter is provided with a shoulder to limit insertion of the tubular member with the tubular member having serrated or roughened surface areas facilitating the gripping of the tubular member by the chuck adapter with the entire structure of the invention being of readily available and relatively inexpensive materials thereby rendering the device economically feasible and providing an effective applicator for many uses.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view of the swab or applicator of the present invention applied to a conventional squeeze bottle.

FIG. 2 is a vertical sectional view, on an enlarged scale, taken substantially along section line 2—2 of FIG. 1 illustrating the specific structural details of this embodiment of the invention.

FIG. 3 is an exploded group perspective view of the components of the invention.

FIG. 4 is an exploded group perspective view of a modified form of the invention in which the chuck adapter is provided with a male threaded lower end.

FIG. 5 is an exploded group perspective view of the chuck adapter having a female threaded lower end.

FIG. 6 is a sectional view similar to FIG. 2 but illustrating the closure disk incorporated therein and associated with a shoulder in the neck of the container.

FIG. 7 is a sectional view illustrating another modified form of the invention similar to FIG. 5 but illustrating the disk in position and illustrating a rigid type of container having a manually operated discharge mechanism such as disclosed in my prior patents.

FIG. 8 is a sectional view similar to the structure in FIG. 4 but also illustrating a rigid container and discharge mechanism.

FIG. 9 is a perspective view of the closure disk for the container.

DESCRIPTION OF THE PREFERRED EMBODIMENTS

Referring now specifically to FIGS. 1–3, the swab or applicator of the present invention is generally designated by the numeral 10 and is mounted on a plastic squeeze bottle 14 by a chuck adapter 16.

The bottle 14 is a conventional squeeze type bottle of any suitable size and configuration for receiving flowable materials such as liquid which can be discharged by squeezing the walls of the bottle towards each other in a well known manner. The bottle 14 includes a top wall 18 provided with an upwardly extending cylindrical neck 20 provided with external spiral screw threads 22 thereon.

The chuck adapter 16 includes a plastic body 24 having a depending cylindrical skirt 26 having a rib or flange 27 thereon which is telescoped into the open upper end of the neck 20 with the rib 27 received in a groove 27a as illustrated in FIGS. 2 and 3 for rotation of adapter 16. A peripheral flange 28 limits the insertion of the skirt 26 into the neck 20 by engaging the upper end thereof. The lower end of the skirt is provided with a peripheral recess 30 and a hollow area 32 extending upwardly from the bottom of the skirt. A longitudinal passageway 34 extends centrally upwardly from the hollow area 32 with the upper end portion of the passageway 34 being slightly larger in diameter as indicated by numeral 36 thus defining an intermediate shoulder 38 at the point of transition from the smaller passageway 34 to the larger upper end of the passageway 36. The external surface of the body 24 above the flange 28 tapers and curves inwardly on the external surface thereof as indicated by numeral 40 and is provided with a plurality of longitudinally extending slits 42 extending from the exterior of the tapered surface 40 to the passageway 36 thereby providing flexible gripping tongues 44 as part of the upper end portion of the body 24.

A tubular cap 46 having an externally serrated lower end portion 48 with a projecting tab 48a thereon is internally screw threaded and is in screwthreaded engagement with the threads 22 on the neck 20 of the bottle 14. The upper portion of the cap 46 curves and tapers inwardly to an opening 50 in the apex thereof with the cap 46 generally conforming in curvature to the tapered or curved surface 40 on the body 24. Thus, when the cap 46 is threaded down onto the neck 20, it will collapse the tongues 44 inwardly to reduce the internal dimensions of the upper end portion 36 of the passageway through the body 24. As illustrated, the tip ends of the tongues 44 which define the passageway 36 actually project up through the opening 50 when the cap 46 is screw threaded onto the neck 20 for gripping the swab 10.

The swab or applicator 10 includes a tubular member 52 of plastic material which is generally rigid but substantially flexible so that it will maintain its substantially straight condition. The tubular member 52 has a longitudinal passageway 54 therethrough and an absorbent swab or tip 56 which is bonded to the tubular member 52 in any suitable manner with the passageway 54 being continuous to the tip end of the swab 56 as indicated by numeral 58. Thus, the passageway 54 is continuous through the absorbent material 56 and actually has a discharge tip end 58. The other end of the tubular member 52 is beveled as at 60 and provided with a roughened external surface area 62 to facilitate the gripping of the tubular member 52 by the tongues 44 so that the cap and body 24 cooperate to securely but releasably grip the tubular member in the passageway 36 with the shoulder 38 engaging the beveled end 60 of the tubular member 52 to limit the insertion of the tubular member 52 so that a substantial length thereof is disposed above the chuck adapter 16 to maintain the desired degree of flexibility thereof.

FIG. 4 illustrates a slightly modified form of the invention in which the cap 46 remains the same as does the body 24. However, in this construction, rather than the container having a neck 20 which is externally threaded, an externally threaded neck 64 becomes an integral part of a depending externally threaded tubular member 66 having a flange 70 with peripheral serrations 72 thereon so that the depending externally threaded tubular member 66 may be threaded into an internally threaded opening in a squeeze bottle or other container. The body 24 is associated with the neck 64 in exactly the same manner as the body 24 is associated with the neck 20 in FIG. 2. Thus, the neck 64, flange 70 and externally threaded tubular member 66 form a male adapter for mounting the chuck adapter on a container having an internally threaded discharge opening or neck thereby increasing the versatility of the device.

FIG. 5 illustrates another embodiment of the invention which is the same as that in FIG. 4 except that in this arrangement, an externally threaded neck 74 which is the same as the neck 64 in FIG. 4 and the neck 20 in FIG. 2 is provided with an internally threaded depending tubular member or female member 76 which is externally serrated at 78 for screw-threaded engagement onto an externally threaded neck on a squeeze bottle or other container. The body 24 and cap 46 are associated with the neck 74 in the same manner as they are associated with the neck 64 in FIG. 4. In both forms of the adapter units as illustrated in FIGS. 4 and 5, the lower end of the adapter is provided with a recess designated by numeral 80 in FIG. 4 and 82 in FIG. 5 for receiving a closure disk generally designated by numeral 84 in both FIGS. 4 and 5. Also, the swab or applicator will be associated with the structures of FIGS. 4 and 5 in exactly the same manner as in FIGS. 1–3.

FIG. 6 illustrates another embodiment of the invention which is substantially the same as that illustrated in FIGS. 1 and 2 with the same reference numerals being applied to the body 24, the cap 46 and the tubular member 52 with these components being associated with each other in the same manner. In this construction, the container 86 includes an externally threaded neck 88 having an outwardly extending peripheral shoulder 90 at the lower end thereof and an inwardly extending shoulder 92 at the lower end thereof which defines a passageway 94 and which forms a support for a closure disk 84 to be described in detail hereinafter. The container 86 may be of rigid construction or of the squeeze type, pressurized in any manner or of any other suitable construction with the closure disk 84 defining a closure for the lower end of the body 24 and the passageways therethrough during periods of non-use thereby enabling the container with the product therein to be stored for relatively long periods of time without any damage thereto which could occur if air could have access to the products. This also prevents leakage of the products in the container and enables the products to be discharged when desired. Also, in FIG. 6, the depending skirt portion 26 of the body is provided with a peripheral rib or flange 27 thereon which sealingly and rotatably engages in groove 27a to secure the body 24 to the neck 88 in the same manner as in the other forms of the invention.

FIG. 7 illustrates a form of the invention similar to FIG. 5 but with the closure disk 84 incorporated therein. In this arrangement, the body 24 is the same as that illustrated in FIG. 6 except that the skirt 26 may be slightly shorter if desired. In this arrangement, the container 96 is provided with an externally threaded neck 98 with the container and neck being rigid and provided with a manually operated mechanism for forcing material from the container 96 with this mechanism being partially illustrated by the screw-threaded shaft 100 disclosed in my previously mentioned patents. In this embodiment, a neck comparable to the neck 74 in FIG. 5 is designated by numeral 102 with the internally threaded depending tubular member 104 being integral therewith and being comparable to the threaded member 76 in FIG. 5 for screw-threaded engagement with the neck 98. The closure disk 84 is received in a recess 106 in a flange 108 that is disposed internally of the adapter unit which is equivalent to the recess 82 in FIG. 5. The closure disk 84 forms a closure for the passageway through the neck 98, the female adapter and into the passageway 34 in the body 24. The association of the body 24, cap 46 and tubular member 52 remain the same in this embodiment of the invention.

FIG. 8 illustrates another embodiment of the invention similar to that illustrated in FIG. 4 with the male adapter being designated by numeral 110 and including a neck 112 that is externally threaded and is equivalent to the neck 64 in FIG. 4 and a depending externally threaded tubular member 114 is provided which is equivalent to the tubular member 66 in FIG. 4. The closure disk 84 is received in a recess 116 equivalent to the recess 80 in FIG. 4 and rests against a flange 118 in the neck 120 of a rigid container 122 which also includes the operating screw-threaded shaft 124 similar to the container illustrated in FIG. 7. The construction of the body 24, cap 46 and tubular member 52 are the same in this embodiment of the invention as in the other embodiments.

FIG. 9 illustrates the details of construction of the closure disk 84 which includes an annular ring 126 and a flat diaphragm or disk 128 of rupturable material with both of these components being constructed of plastic or equivalent material. Thus, the closure disk 84 provides a seal for the contents of the container with the closure disk being rupturable by the pressure exerted on the contents or manually rupturable if desired. The disk 84 may be snapped into its recess, frictionally held therein or adhesively bonded thereto. The tab or projecting lug 48a makes it easier to turn the cap 46 when gripping or releasing the swab 52. There is a reduction of effort required to operate the chuck adapter since there is no relative rotational movement between the cap 46, the grippers 42 and swab 52. Thus the tab 48a or ear like projection can be easily swung a partial turn to cause radial movement of the gripping tongues 42.

This occurs since grippers 42 swivel with respect to the neck 20 in which 42 is telescopically received, since said grippers 42 are integral with dome shaped part 40 and skirt 26. The skirt has peripheral shoulders 27 and 28 with shoulder 27 swivel set or snapped into accommodating circular recess 27a of neck 20. It can now be readily seen that such engagement permits aforementioned part 24 containing grippers 42 to rotate in a prescribed circular motion. This motion in concert with rotation of cap 46 is due to flexible-fit-tightness between interior of part 46 about-and-upon grippers 42 and dome part 40. Actually there is tightening and holding of swab 52 when pressure originates by part 50 of cap 46 at the moment this cap 46 is rotated in one prescribed direction. This is due to flexibility of grippers 42 as they are influenced by part 50 to compress and grip. The reverse is so when cap 46 is rotated in the opposite direction, thereby releasing the swab 52, with the flexibility and resiliency of grippers 42 again coming into play.

The swivel of grippers provides another significant advantage since the construction aforementioned acts to contain contents without leakage allowing communication of contents through hollow canal 54 and through end opening 58 of swab 52 throughout the sequence of operation.

The components may be constructed of readily available plastic materials and by using conventional and well known techniques the cost may be retained at a minimum. The materials may be any suitable color in order to provide an attractive assembly. Also, if desired, the annular groove or recess which normally receives the annular ring 126 of the rupturable closure disk 84 can be filled with an annular ring without a membrane 128 when a closure disk is not used in order to provide a smooth interior surface to the passageway defined by the interior of the components of the applicator thereby eliminating the possibility of material being deposited in these areas.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to falling within the scope of the invention.

What is claimed as new is as follows:

1. An applicator comprising a tubular member having a swab on one end thereof with the swab enclosing only a minor portion of the length of the tubular member and projecting slightly beyond said one end of the tubular member whereby the swab is supported solely by the tubular member, the other end of the tubular member being open, said tubular member and swab having a passageway extending completely therethrough and terminating at the outer end of the swab to provide an uninterrupted, continuous passageway through the tubular member and swab for applying material to a surface, said tubular member being constructed of shape-sustaining material having sufficient flexibility to enable bending during application of material to a surface.

2. The structure as defined in claim 1, and means mounting the tubular member on the container including an adapter in the form of a chuck body having a passageway extending therethrough telescopically receiving the open end of the tubular member, a cap on the body for movement toward and away from the container, said body having longitudinal slits therein terminating at its outer end, said body and cap having correspondingly tapered surfaces for collapsing the outer end of the body into gripping engagement with the tubular member when the cap is moved towards the container, said chuck body including a rupturable closure disk forming a closure for the container, said cap being screw threaded to the container for selectively gripping the tubular member, and means securing the chuck body to the container including a skirt portion on the chuck body telescopically received by a neck on the container.

3. An applicator comprising a tubular member having a swab on one end thereof, said tubular member having a passageway extending completely therethrough and terminating at the outer end of the swab to provide an unterrupted, continuous passageway through the tubular member and swab for applying material to a surface, said tubular member being constructed of shape-sustaining material having sufficient flexibility to enable bending during application of material to a surface, means mounting the tubular member on the container including an adapter in the form of a chuck body having a passageway extending therethrough telescopically receiving the end of the tubular member, a cap on the body for movement toward and away from the container, said body having longitudinal slits therein terminating at its outer end, said body and cap having correspondingly tapered surfaces for collapsing the outer end of the body into gripping engagement with the tubular member when the cap is moved towards the container, said body including a peripheral limit shoulder in the central portion of the passageway therethrough for limiting the insertion of the tubular member, said tubular member including a serrated peripheral surface on the inner end thereof to facilitate gripping of the tubular member by the chuck body, said tubular member and body being constructed of plastic material, said body including means securing it to a neck portion of a container of the squeeze bottle type or dispensing type, said chuck body including a closure means therein forming a closure for a container to retain the contents thereof in sealed condition during periods of non-use, said closure means being in the form of a disk of rupturable material forming a closure for the container and being rupturable by pressure exerted on the contents of the container, said cap being provided with screw-threaded connection with the neck of a container at the end thereof remote from the tapered surface, said means securing the chuck body to the neck of a container including a depending skirt and an internal peripheral groove formed in the neck of the container receiving the rib for locking the chuck body in the neck of the container, said cap including a laterally projecting tab on the screw-threaded portion to facilitate rotation of the cap in relation to the neck of the container.

4. An applicator comprising a tubular member having a swab on one end thereof, said tubular member having a passageway extending completely therethrough and terminating at the outer end of the swab to provide an uninterrupted, continuous passageway through the tubular member and swab for applying material to a surface, said tubular member being constructed of shape-sustaining material having sufficient flexibility to enable bending during application of material to a surface, means mounting the tubular member on the container including an adapter in the form of a chuck body having a passageway extending therethrough telescopically receiving the end of the tubular member, a cap on the body for movement toward and away from the container, said body having longitudinal slits therein terminating at its outer end, said body and cap having correspondingly tapered surfaces for collapsing the outer end of the body into gripping engagement with the tubular member when the cap is moved towards the container, said body including a peripheral limit shoulder in the central portion of the passageway therethrough for limiting the insertion of the tubular member, said tubular member including a serrated peripheral surface on the inner end thereof to facilitate gripping of the tubular member by the chuck body, said tubular member and body being constructed of plastic material, said body including means securing it to a neck portion of a container of the squeeze bottle type or dispensing type, said chuck body including a closure means therein forming a closure for a container to retain the contents thereof in sealed condition during periods of non-use, said closure means being in the form of a disk of rupturable material forming a closure for the container and being rupturable by pressure exerted on the contents of the container, said means securing the chuck body to the neck of a container including an adapter having screw-threaded engagement with the neck of the container, said chuck body including a depending skirt telescoped into the adapter and provided with a peripheral rib thereon received in a peripheral groove in the adapter, said cap including a screw-threaded end portion threaded onto the adapter, and a laterally extending tab on the cap adjacent the screw-threaded portion thereof to facilitate rotation of the cap.

5. The structure as defined in claim 3 wherein said chuck body includes a peripheral rib engaged with the top edge of the neck of the container for anchoring the body to the neck of the container.

6. The structure as defined in claim 4 wherein said chuck body includes a peripheral external rib engaging the top edge of the adapter, said disc of rupturable material being mounted in said adapter.

* * * * *